United States Patent [19]

Zhao

[11] Patent Number: 5,602,267

[45] Date of Patent: Feb. 11, 1997

[54] ORGANOMETALLIC CATALYSTS FOR EPOXIDIZING PROCHIRAL OLEFINS AND A NEW CLASS OF AMID-SALICYLIDENE LIGANDS

[75] Inventor: Shu-Hai Zhao, Corpus Christi, Tex.

[73] Assignee: Hoechst Celanese, North Somerville, N.J.

[21] Appl. No.: 450,739

[22] Filed: May 26, 1995

[51] Int. Cl.⁶ .............................. C07F 13/00; C07F 7/00; C07F 11/00; C07F 5/00
[52] U.S. Cl. .................. 556/45; 556/7; 556/13; 556/42; 556/51; 556/57; 556/113; 556/117; 556/137; 556/146; 556/150; 534/14; 534/15; 424/9.3
[58] Field of Search .................... 549/523; 556/7, 556/13, 45, 42, 51, 57, 113, 137, 146, 150, 50; 534/10, 14, 15; 424/1.65, 9.3, 9.363

[56] References Cited

U.S. PATENT DOCUMENTS 5,352,814  10/1994  Katsuki et al. .................... 556/50

OTHER PUBLICATIONS

Corman et al., Inorg. Chem., vol. 34, No. 16, pp. 4213–4219, (1995).

*Primary Examiner*—Gary E. Hollinden
*Assistant Examiner*—Michael G. Hartley
*Attorney, Agent, or Firm*—James J. Mullen

[57] ABSTRACT

Asymmetric synthesis using a novel catalyst comprising the formula:

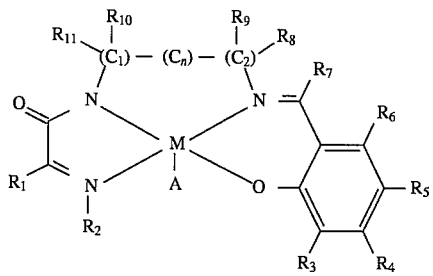

and which has utility in areas such as epoxidation of olefins.

40 Claims, No Drawings

ORGANOMETALLIC CATALYSTS FOR EPOXIDIZING PROCHIRAL OLEFINS AND A NEW CLASS OF AMID-SALICYLIDENE LIGANDS

BACKGROUND OF THE INVENTION

1. Field of the Invention

The present invention relates to the field of asymmetric catalysis. More particularly, the invention relates to the field of organometallic catalysts useful for enantioselectively epoxidizing prochiral olefins and a new class of amid-salicylidene ligands and their metal complexes (i.e. an optically active metal ligand complex catalyst) as novel ligands and novel catalysts.

Asymmetric epoxidation of olefins constitutes an extremely appealing strategy for the synthesis of optically active organic compounds. Several advances in this area have occurred in recent years. The most commonly and successfully used catalysts for asymmetric epoxidation of unfunctionalized olefins are porphyrin and salen based systems. Chiral metal porphyrins have been reported to catalyze asymmetric epoxidation of styrene derivatives with high turnover numbers and moderate enantioselectivities (J. P. Collman et al. *Science*, 1993, 26, 1404). Unfortunately, the chiral porphyrin systems are usually difficult to prepare and are limited to styrene derivatives as substrates. E. N. Jacobsen (*J. Am. Chem. Soc.* 1990, 112, 2801) and T. Katssuki (Tetrahedron Lett. 1990, 31, 7345) independently reported asymmetric epoxidation of olefins by bleach or iodosobenzene catalyzed by chiral manganese salen complexes. These chiral salen complexes were designed based on Kochi's achiral cationic mangangese salen complex that was reported in 1986 (*J. Am. Chem. Soc.* 1986, 108, 108, 2309). The salen based catalysts gave very high enantioselectivities for the epoxidation of cis olefins, e.g. cis-beta-methylstyrene and dihydronaphthalene. However, the turnover numbers of these catalysts are typically 10–30, and they are limited to conjugated cis olefins.

Given the broad synthetic utility of chiral epoxides, more efficient catalytic and enantioselective catalysts besides porphyrin and salen systems for asymmetric epoxidation of unfunctionalized olefins are clearly desirable.

2. Description of the Prior Art

The following prior art references are disclosed in accordance with the terms of 37 CFR 1.56, 1.97, and 1.93.

U.S. Pat. No. 4,471,130 discloses methods for asymmetric epoxidation of allylic alcohols.

U.S. Pat. No. 4,594,439 discloses methods for asymmetric epoxidation of carbinals using a titanium catalyst.

U.S. Pat. No. 4,924,011 discloses a process for preparing taxol.

U.S. Pat. No. 5,352,814 discloses methods for asymmetric epoxidation of olefins using an optically active manganese complex.

PCT WO 93/03838 (published Mar. 4, 1993) discloses chiral catalysts useful for epoxidizing prochiral olefins.

PCT WO 93/12260 (published Jun. 24, 1993) discloses a class of asymmetric ligands preferably derived from 2-diphenylphosphinobenzoic acid as an ester or amide from chiral alcohols and chiral amines.

Journal of American Chemical Society, Vol. 110, pages 4087–4089, issued 1988 (ACS), Yoon et al., discloses "Catalysis of Alkene Oxidation by Nickel Salen Complexes Using NaOCl under Phase-Transfer Conditions".

Coordination Chemistry Reviews 140, (1995) pp. 189–214, T. Katsuki; Elsevier Science S.A. discloses salen-manganese complexes as catalysts for asymmetric oxidations of unfunctionalized olefins.

Catalytic Asymmetric Synthesis, Iwao Ojima—Editor (1993), VCH Publishers, Inc., pp. 159–202; "Asymmetric Catalytic Epoxidation of Unfunctionalized Olefins" by Eric N. Jacobsen discloses salen-manganese complexes as catalysts for asymmetric oxidations of unfunctionalized olefins.

Journal of American Chemical Society, Vol. 112, No. 7, pages 2801–2803, issued Mar. 28, 1990 (ACS), Zhang et al., discloses "Enantioselective Epoxidation of Unfunctionalized Olefins Catalyzed by (Salen) Manganese Complexes".

Journal of American Chemical Society, Vol. 113, No. 18, pages 7062–4, issued Aug. 28, 1991 (ACS), Jacobsen et al., discloses "Highly Enantioselective Epoxidation Catalysts Derived from 1,2-Diaminocyclohexane".

Bulletin Chemical Society of Japan, Vol. 56, No. 1, issued January, 1983, Kanatomi, discloses "The Dehydrogenation of Nickel (II) Chelates of rac- and meso-2,2'-[(1,2-Diphenylethylene)bis(iminomethylene)diphenol and Related Compounds".

Chemistry Letters, issued 1986, pages 1483–6 (The Chemical Society of Japan), Nakajima et al., discloses "Asymmetric Oxidation of Sulfides to Sulfoxides by Organic Hydroperoxides with Optically Active Schiff Base—Oxovanadium (IV) Catalysts".

Journal of American Chemical Society, Vol. 113, No. 17, pages 6703–4, issued Aug. 14, 1991 (ACS), Jacobsen et al., discloses "Electronic Tuning of Asymmetric Catalysts".

All of the above-cited prior art and any other references mentioned herein are incorporated herein by reference in their entirety.

SUMMARY OF THE INVENTION

The present invention provides a novel catalyst having the formula:

wherein M, A, R, $(C_1)$, $(C_n)$, and $(C_2)$ are defined herein. Such catalyst has unique utility in areas such as epoxidation of olefins, particularly unfunctionalized olefins.

DETAILED DESCRIPTION OF THE INVENTION

In one facet of the present invention, there is provided new and novel ligands having the general formula:

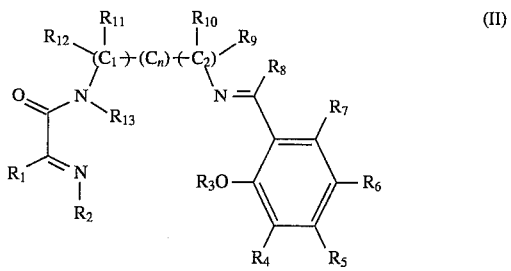
(II)

In this formula II, $R_1$ and $R_2$ are independently selected from the group consisting of hydrogen; alkyl $C_1$–$C_{50}$; substituted and unsubstituted phenyl, naphthyl, and anthracyl; and a cyclic ring encompassing both $R_1$ and $R_2$ and containing a total of 3 to 50 atoms selected from the group consisting of carbon atoms, oxygen atoms, nitrogen atoms, sulfur atoms; and mixtures thereof, with the proviso that the substituents on the alkyl, phenyl, naphthyl, anthracyl, and cyclic rings can be nitro, halogen, alkoxy, carboxylate, amino, amide, silyl, and siloxyl; $R_3$ is selected from the group consisting of hydrogen and alkyl $C_1$–$C_{20}$. $R_3$ and $R_4$ are independently selected from the group consisting of substituted and unsubstituted alkyl and aryl; nitro; halogen; hydrogen; alkoxy; carboxylate; amino; amide; silyl; and siloxyl. $R_4$ and $R_5$, $R_5$ and $R_6$, and R and $R_7$ may also (in addition to the above) form a cyclic ring containing a total of 2 to 6 atoms selected from the group consisting of carbon atoms, oxygen atoms, nitrogen atoms, sulfur atoms, and mixtures thereof and said ring can be substituted or unsubstituted.

$R_{10}$ and $R_{11}$ are independently selected from the group consisting of hydrogen, alkyl $C_1$–$C_{20}$, substituted and unsubstituted phenyl, naphthyl, and anthracyl, and a cyclic ring encompassing both $R_{10}$ and $R_{11}$ and containing a total of 2 to 6 atoms selected from the group consisting of carbon atoms, oxygen atoms, nitrogen atoms, sulfur atoms, and mixtures thereof. n is either 0, 1, or 2; and ($C_1$), ($C_n$), and ($C_2$) are independently or jointly part of an unsubstituted or substituted aryl group.

In another facet of the present invention, there is provided new and novel catalysts having the general formula:

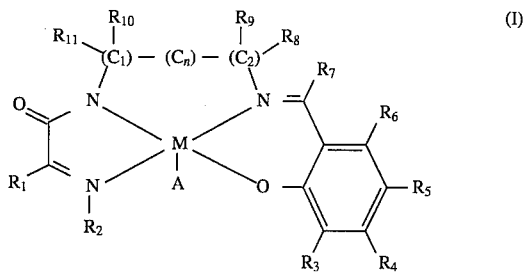
(I)

wherein in formula I above, $R_1$–$R_{11}$ have the same meaning as set forth in formula II. Additionally, in this formula I, the following definitions apply:

M is a transition metal ion and includes such metals as manganese, cobalt, nickel, chromium, iron, rhenium, ruthenium, rhodium, technetium, palladium, platinum, osmium, copper, tellurium, titanium, vanadium, molybdenum, and gadolinium; and A is an anion and includes halides (chlorine, fluorine, bromine, and iodine); carboxylates; $PF_6$; $BF_4$; $B(R)_4$; and R wherein R is either a substituted or unsubstituted alkyl or aryl; acetates; sulfonates; triflates; and tosylates.

A is not present when the metal selected for M has an oxidation state of two or less. Thus, if the metal selected for M is, for example, nickel (II), then the catalyst structural formula would be as follows:

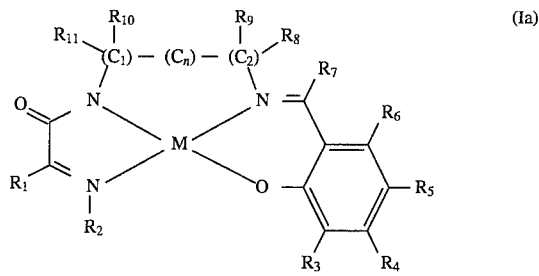
(Ia)

Furthermore, the entire complex of Formula I can have positive or negative charges from e.g. +3 to −2, depending upon the metal selected for M. The complex of formula I can be in its hydrated form or coordinated with one or more axial ligands. These axial ligands include alcohols, ketones, and substituted or unsubstituted amines or pyridines and their N-oxides.

As used herein, the term "substituted" is contemplated to include all permissible substitutents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substitutents of organic compounds described herein which satisfy the valencies of the heteroatoms. This invention is not intended to be limited in any manner by the permissible substituents of organic compounds.

The novel catalysts falling within formula I above may or may not have chiral carbon centers at ($C_1$) or ($C_2$). In certain cases, it has been found advantageous to have at least one chiral carbon center at ($C_1$) and ($C_2$).

Examples of the combination of "R" groups such as $R_1$ and $R_2$, wherein there is found a cyclic ring, include the following:

(a)

(b)

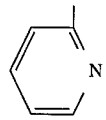 (c)

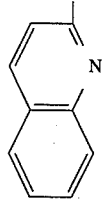 (d)

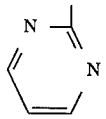 (e)

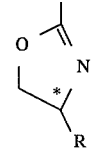

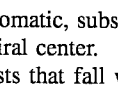

where R is alkyl or aromatic, substituted, or unsubstituted; and * connotates a chiral center.

Examples of catalysts that fall within formula I include the following:

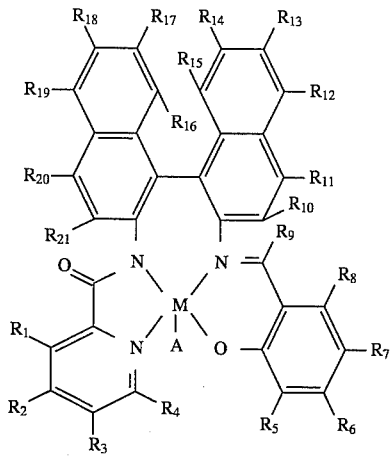 (III)

wherein M is a transition metal ion; A is an anion; and $R_1$–$R_{21}$ are independently selected from the group consisting of substituted and unsubstituted alkyl and aryl groups; nitro; hydrogen; halogen; alkoxy; carboxylate; amino; amide; silyl; and siloxyl.

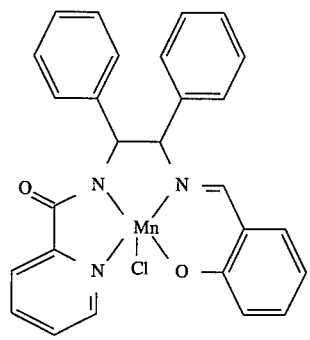 (IV)

 (V)

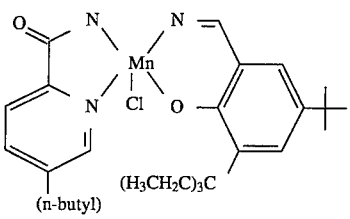

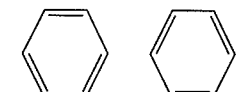 (VI)

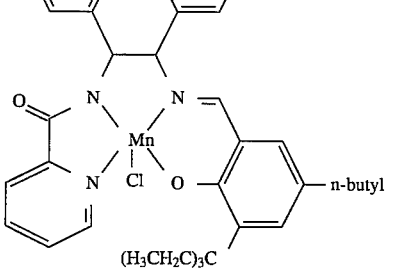

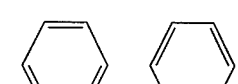 (VII)

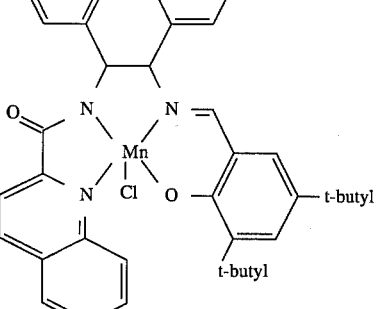

 (VIII)

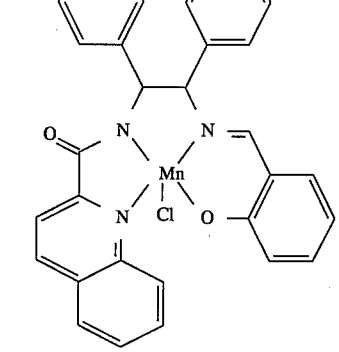

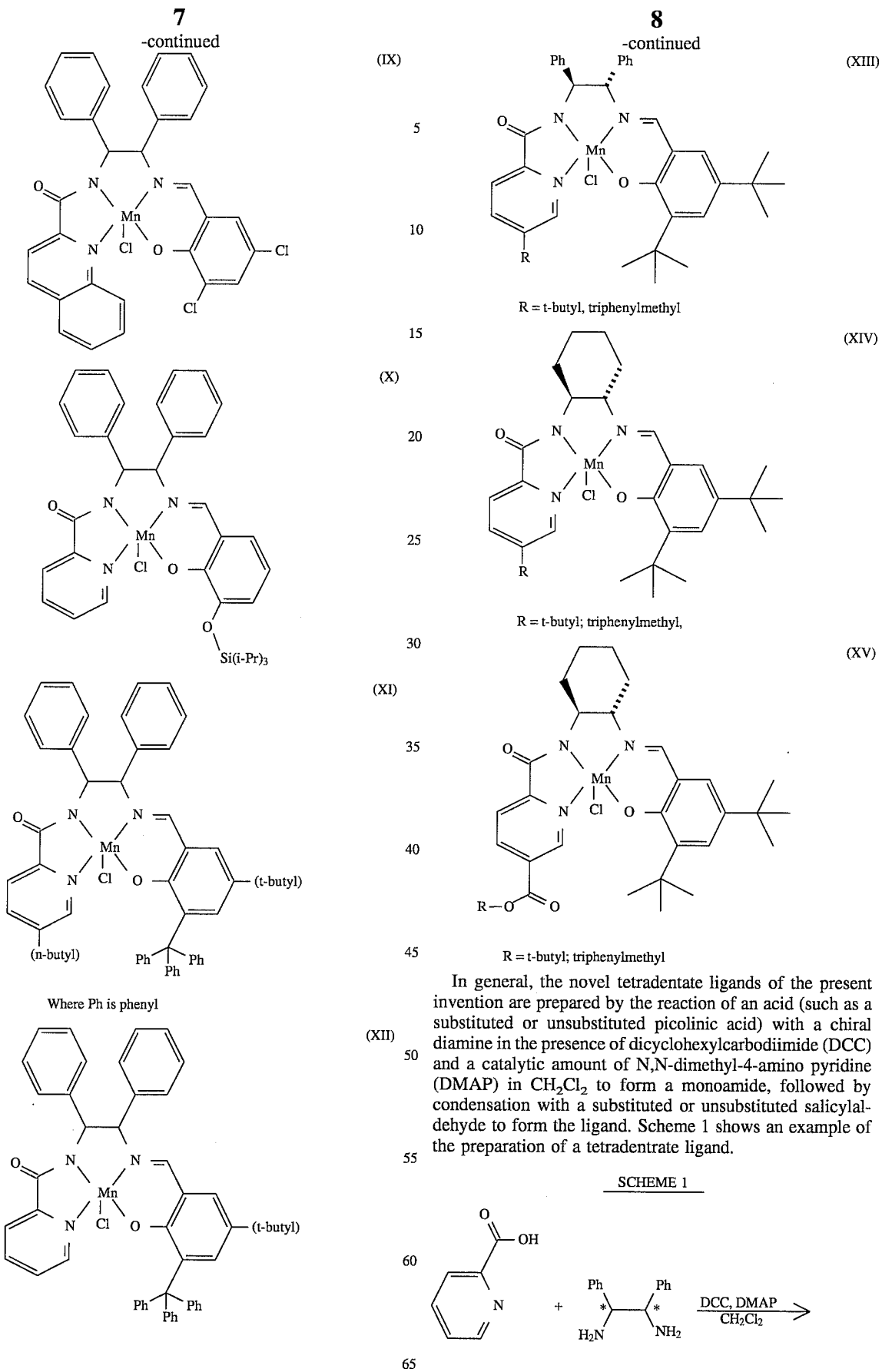

In general, the novel tetradentate ligands of the present invention are prepared by the reaction of an acid (such as a substituted or unsubstituted picolinic acid) with a chiral diamine in the presence of dicyclohexylcarbodiimide (DCC) and a catalytic amount of N,N-dimethyl-4-amino pyridine (DMAP) in $CH_2Cl_2$ to form a monoamide, followed by condensation with a substituted or unsubstituted salicylaldehyde to form the ligand. Scheme 1 shows an example of the preparation of a tetradentrate ligand.

-continued
SCHEME 1

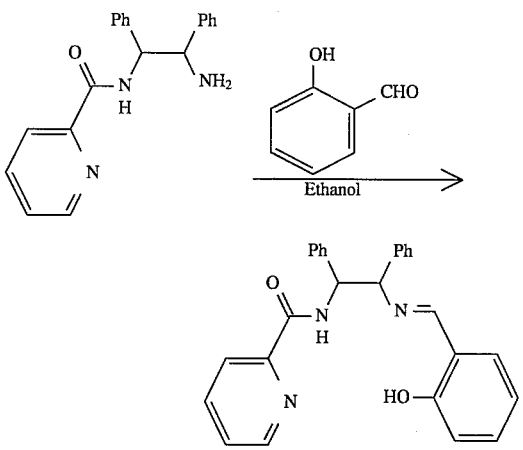

The novel catalysts of the present invention are prepared by reacting the ligand with, for example, Mn(OAc)$_3$ and LiCl in an organic liquid/solvent such as ethanol. The catalyst in this example has the structure as shown above in formula IV.

This facet of the present invention relates to asymmetric syntheses in which a prochiral or chiral compound is reacted in the presence of optically active, metal-ligand complex catalyst, in enantiomerically active form, to produce an optically active product.

Specifically, it has been unexpectedly found that the general catalyst, disclosed in the earlier part of this specification, can effect asymmetric synthesis in various processes with various substrates to produce a material which is optically active.

The asymmetric syntheses processes of this invention are useful for the production of numerous optically active organic compounds, e.g., epoxides, sulfoxides, aziridines, cyclopropanes, aldehydes, alcohols, ethers, esters, amines, amides, carboxylic acids and the like, which have a wide variety of applications.

This part of the subject invention encompasses the carrying out of any known conventional syntheses in an asymmetric fashion with the novel optically active metal-ligand complex catalyst as disclosed herein. As indicated above, the processes of this invention stereoselectively produce an enantiomer. Preferred asymmetric syntheses reactions involve the reaction of organic compounds with an oxygen atom source in the presence of a catalytic amount of an optically active metal-ligand complex catalyst.

More preferably, the subject invention relates to asymmetric epoxidation which involves the use of an optically active metal-ligand complex catalyst in the production of optically active epoxides wherein a prochiral or chiral olefinic compound is reacted with an oxygen atom source. The processing techniques of this invention may correspond to any of the known processing techniques heretofore employed in conventional asymmetric synthesis reactions including asymmetric epoxidation reactions.

For instance, the asymmetric synthesis processes can be conducted in continuous, semi-continuous, or batch fashion and involve a liquid recycle and/or gas recycle operation as desired. Likewise, the manner or order of addition of the reaction ingredients, catalyst, and solvent are also not critical and may be accomplished in any conventional fashion.

In general, the asymmetric syntheses reactions are carried out in a liquid reaction medium that contains a solvent for the optically active catalyst, preferably one in which the reaction ingredients, including catalyst, are substantially soluble.

As indicated above, the subject invention encompasses the carrying out of any known conventional syntheses in an asymmetric fashion in which the catalyst thereof is replaced by an optically active metal-ligand complex as disclosed herein.

Asymmetric oxidation of sulfides to sulfoxides can be carried out in accordance with conventional procedures known in the art. For example, sulfides can be converted to optically active sulfoxides under oxidation conditions in the presence of an optically active metal-ligand complex catalyst described herein.

Asymmetric oxidation of aldehydes to acids can be carried out in accordance with conventional procedures known in the art. For example, optically active acids can be prepared by reacting a racemic aldehyde and an oxygen atom source in the presence of an optically active metal-ligand complex catalyst described herein.

Asymmetric hydrocyanation can be carried out in accordance with conventional procedures known in the art. For example, optically active nitrile compounds can be prepared by reacting a prochiral olefinic and hydrogen cyanide under hydrocyanation conditions in the presence of an optically active metal-ligand complex catalyst described herein.

Asymmetric olefin hydrosilylation can be carried out in accordance with conventional procedures known in the art. For example, optically active silyl compounds can be prepared by reacting a prochiral olefin and a silyl compound under hydrosilylation conditions in the presence of an optically active metal-ligand complex catalyst described herein.

Asymmetric ketone hydrosilylation can be carried out in accordance with conventional procedures known in the art. For example, optically active silyl ethers or alcohols can be prepared by reacting a prochiral ketone and a silyl compound under hydrosilylation conditions in the presence of an optically active metal-ligand complex catalyst described herein.

Asymmetric aziridination can be carried out in accordance with conventional procedures known in the art. For example, prochiral olefins can be converted to optically active aziridines under aziridanation conditions in the presence of an optically active metal-ligand complex catalyst described herein.

Asymmetric hydroamidation can be carried out in accordance with conventional procedures known in the art. For example, optically active amides can be prepared by reacting a prochiral olefin, carbon monoxide, and a primary or secondary amine or ammonia under hydroamidation conditions in the presence of an optically active metal-ligand complex catalyst described herein.

Asymmetric olefin hydrogenations and other asymmetric hydrogenations can be carried out in accordance with conventional procedures known in the art. For example, hydrogenation can be used to reduce a carbon-carbon double bond to a single bond. Other double bonds can also be hydrogenated, for example, a ketone can be converted to an optically active alcohol under hydrogenation conditions in the presence of an optically active metal-ligand complex catalyst described herein.

Asymmetric aminolysis can be carried out in accordance with conventional procedures known in the art. For example, optically active amines can be prepared by reacting a prochiral olefin with a primary or secondary amine under aminolysis conditions in the presence of an optically active metal-ligand complex catalyst described herein.

Asymmetric isomerization can be carried out in accordance with conventional procedures known in the art. For example, allylic alcohols can be isomerized under isomerization conditions to produce optically active aldehydes in the presence of an optically active metal-ligand complex catalyst described herein.

Asymmetric Grignard cross coupling can be carried out in accordance with conventional procedures known in the art. For example, optically active products can be prepared by reacting a chiral Grignard reagent with an alkyl or aryl halide under Grignard reagent with an alkyl or aryl halide under Grignard cross coupling conditions in the presence of an optically active metal-ligand complex catalyst described herein.

Asymmetric transfer hydrogenation can be carried out in accordance with conventional procedures known in the art. For example, optically active alcohols can be prepared by reacting a prochiral ketone and an alcohol under transfer hydrogenation conditions in the presence of an optically active metal-ligand complex catalyst described herein.

Asymmetric olefin hydroboration can be carried out in accordance with conventional procedures known in the art. For example, optically active alkyl boranes or alcohols can be prepared by reacting a prochiral olefin and a borane under hydroboration conditions in the presence of an optically active metal-ligand complex catalyst described herein.

Asymmetric olefin cyclopropanation can be carried out in accordance with conventional procedures known in the art. For example, optically active cyclopropanes can be prepared by reacting a prochiral olefin and a diazo compound under cyclopropanation conditions in the presence of an optically active metal-ligand complex catalyst described herein.

Asymmetric aldol condensations can be carried out in accordance with conventional procedures known in the art. For example, optically active aldols can be prepared by reacting a prochiral ketone or aldehyde and a silyl enol ether under aldol condensation conditions in the presence of an optically active metal-ligand complex catalyst described herein.

Asymmetric olefin codimerization can be carried out in accordance with conventional procedures known in the art. For example, optically active hydrocarbons can be prepared by reacting a prochiral alkene and an alkene under codimerization conditions in the presence of an optically active metal-ligand complex catalyst described herein.

Asymmetric allylic alkylation can be carried out in accordance with conventional procedures known in the art. For example, optically active hydrocarbons can be prepared by reacting a prochiral ketone or aldehyde and an allylic alkylating agent under alkylation conditions in the presence of an optically active metal-ligand complex catalyst described herein.

Asymmetric Diels-Alder reaction can be carried out in accordance with conventional procedures known in the art. For example, optically active olefins can be prepared by reacting a prochiral diene and an olefin under cycloaddition conditions in the presence of an optically active metal-ligand complex catalyst described herein.

The permissible prochiral and chiral starting material reactants encompassed by the processes of this invention are, of course, chosen depending on the particular asymmetric synthesis desired. Such starting materials are well known in the art and can be used in conventional amounts in accordance with conventional methods. Illustrative starting material reactants include, for example, substituted and unsubstituted aldehydes (intramolecular hydroacylation, aldol condensation, oxidation to acids, prochiral olefins (epoxidation, hydrocyanation, hydrosilylation, aziridination, hydroamidation, aminolysis, cyclopropanation, hydroboration, Diels-Alder reaction, codimerization), ketones (hydrogenation, hydrosilylation, aldol condensation, transfer hydrogenation, allylic alkylation), epoxides (hydrocyanation, nucleophilic ring opening reaction), alcohols (carbonylation) acyl and aryl chlorides (decarbonylation), a chiral Grignard reagent (Grignard cross coupling) and the like.

The novel catalysts of the present invention thus have utility in a wide variety of chemical processes, and particularly, in asymmetric synthesis reaction which include, without limitation, epoxidation; hydroxylation; cyclopropanation; aziridination; Diels-Alder reactions; cycloaddition, Michael addition; Aldol reaction; hydroboration; olefin and ketone hydrosilylation; hydrocyanation; addition of Grignards or organometallics to aldehydes and ketones; allylic alkylation; Grignard cross coupling; kinetic resolution; oxidation of aldehydes, hydroamidation; olefin isomerization; aminolysis; hydrogenation; hydrocarboxylation; oxidation of sulfides; oxidation of phosphines; and oxidation of selenides.

While the present invention catalysts have the above illustrated uses, the general discussion herein will focus around the epoxidation of olefins, particularly unfunctionalized olefins.

Illustrative olefin starting material reactants useful in certain of the asymmetric synthesis processes of this invention, e.g. epoxidation, include those which can be terminally or internally unsaturated and be of straight chain, branched chain, or cyclic structure. Such olefins can contain from 3 to 40 carbon atoms or greater and may contain one or more ethylenic unsaturated groups. Moreover, such olefins may contain groups or substituents which do not essentially adversely interfere with the asymmetric synetheses process such as carbonyl, carbonyloxy, oxy, hydroxy, oxycarbonyl, halogen, alkoxy, aryl, haloalkyl, and the like. Illustrative olefinic unsaturated compounds include substituted and unsubstituted alpha olefins, internal olefins, alkyl alkenoates, alkenyl alkanoates, alkenyl alkyl ethers, alkenols, and the like, e.g. 1-butene, 1-pentene, 1-hexene, 1-octene, 1-decene, 1-dodecene, 1-octadecene, 2-butene, isoamylene, 2-pentene, 2-hexene, 3-hexene, 2-heptene, cyclohexene, propylene dimers, propylene trimers, propylene tetramers, 2-ethylhexene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, aryloates such as vinyl benzoate and the like, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, substituted and unsubstituted chromenes, 3-butenenitrile, 5-hexenamide, styrene, indene, 1,2-dihydronaphthalene, norbornene, alpha-methylstyrene, and the like. Illustrative preferred olefinic unsaturated compounds include, for example, p-isobutylstyrene, 2-vinyl-6-methoxynaphthylene, 3-ethenylphenyl phenyl ketone, 4-ethylphenyl-2-thienylketone, 4-ethenyl-2-fluorobiphenyl, 4-(1m,3-dihydro-1-oxo-2H-isoindol-2-yl)styrene, 2-ethyl-5-benzoylthiophene, 3-ethenylphenyl phenyl ether, propenylbenzene, isobutyl-4-propenyl-benzene, phenyl vinyl ether, vinyl chloride, and the like. Suitable olefinic unsaturated compounds useful in certain asymmetric syntheses processes of this invention include substituted aryl ethylenes described in U.S. Pat. No. 4,329,507, incorporated herein by reference in its entirety. Of course, it is understood that mixtures of different olefinic starting materials can be employed, if desired, by the asymmetric syntheses processes of the subject invention. More preferably, the subject invention is especially useful for the production of optically active materials, by epoxidation of alpha olefins containing from 3 to 40 carbon atoms or greater, as well as starting material mixtures of such alpha olefins and internal olefins.

Illustrative prochiral and chiral olefins useful in the processes of this invention include those represented by the formula:

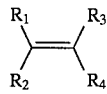

wherein $R_1$, $R_2$, $R_3$, and $R_4$ are the same or different (provided $R_1$ is different from $R_2$ and $R_3$ is different from $R_4$) and are selected from hydrogen; alkyl; substituted alkyl, said substitution being selected from amino including alkyamino and dialkylamino, such as benzylamino and dibenzylamino, hydroxy, alkoxy, such as methoxy and ethoxy, acyloxy, such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino; hydroxy, alkoxy such as methoxy and ethoxy, acyloxy such as acetoxy, halo, nitrile, nitro, carboxyl, carboxaldehyde, carboxylic ester, carbonyl, and thio, said aryl substitution being less than four substituents; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto.

It is understood that the prochiral and chiral olefins of this definition also include molecules of the above general formula where the R-groups are connected to form ring compounds, e.g., 2-methyl-1-cyclohexene, and the like.

In accordance with the epoxidation process of the present invention, the prochiral olefin, an oxygen atom source, and the chiral catalyst are reacted under such conditions and for such time as is needed to epoxidize said olefin. In addition to those olefins set forth above, the prochiral olefin can be selected from mono-substituted, 1,1-disubstituted, cis-1,2-disubstituted, trans-1,2-disubstituted, trisubstituted, and tetrasubstituted. Of these, the monosubstituted and cis-1,2-disubstituted have shown the highest ee values.

Preferably, the prochiral olefin to be epoxidized is selected from the group consisting of cis-disubstituted olefins, including cyclic olefins, bearing a sterically demanding substituent on one end and a smaller substituent on the other end. More preferably, the prochiral olefin is a cis disubstituted olefin with a primary substituent on one side of the double bond and a second, tertiary, or aryl substituent on the other side.

The prochiral olefin can also be selected from the group consisting of enamines, enols, and alpha, beta-unsaturated carbonyls. More preferably, the prochiral olefin is selected from the group consisting of cis-β-methyl-styrene, dihydronaphthalene, 2-cyclohexenyl-1,1-dioxolane, propylene, styrene, and 2,2-dimethylcyclochromene. Most preferably, the prochiral olefin is cis-β-methylstyrene.

The oxygen atom source used in the epoxidation reaction should be an oxidant which is relatively unreactive toward olefins under mild conditions. Preferably, the oxygen atom source is selected from the group consisting of NaOCl, iodosylmesitylene, $NaIO_4$, $NBu_4IO_4$, potassium peroxymonosulfate, magnesium monoperoxyphthalate, and hexacyanoferrate ion. More preferably, the oxygen atom source is selected from the group consisting of NaOCl and iodosomesitylene. For economic reasons, the most preferred oxygen atom source is NaOCl. Thus, a preferred method uses NaOCl as the oxygen atom source.

The amount of optically active complex catalyst in the reaction medium of a given process of this invention need only be that minimum amount necessary to catalyze the particular asymmetric syntheses process desired. In general, concentrations in the range of from about 1 ppm to about 10,000 ppm, based on the starting reactant, should be sufficient for most asymmetric syntheses processes. For example, in the catalyzed asymmetric epoxidation processes of this invention, it is generally preferred to employ from about 10 to 1000 ppm and more preferably from 25 to 750 ppm.

The process conditions employable in the asymmetric processes of this invention are, of course, chosen depending on the particular asymmetric syntheses desired. Such process conditions are well known in the art. All of the asymmetric syntheses processes of this invention can be carried out in accordance with the conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference in their entirety. Depending on the particular process, operating temperatures can range from about −80° C. or less to about 500° C. or greater and operating pressures can range from about 1 psia or less to about 10,000 psia or greater.

The reaction conditions of effecting, for example, the asymmetric epoxidation process of this invention may be those heretofore conventionally used and may comprise a reaction temperature of from about −25° C. or lower to about 200° C. or higher and pressures ranging from about 1 to about 10,000 psia. While one example of the asymmetric syntheses process is the epoxidation of olefinically unsaturated compounds and more preferably olefinic hydrocarbon, to produce optically active epoxides, it is to be understood that the optically active metal-ligand complexes may be employed as catalysts in other types of asymmetric syntheses processes to obtain good results. Moreover, while such other asymmetric syntheses may be performed under their usual conditions, in general, it is believed that they may be performed at lower temperatures than normally preferred due to the optically active metal-ligand complex catalysts.

The total gas pressure of the oxygen atom source and, for example, olefinic unsaturated starting compound of one asymmetric (epoxidation) process of this invention may range from about 1 to about 10,000 psia. More preferably, however, in the asymmetric epoxidation of prochiral olefins to produce optically active epoxides, it is preferred that the process be operated at a total gas pressure of less than about 150 psia, and more preferably less than about 1000 psia. The minimum total pressure of the reactants is not particularly critical and is limited predominately only by the amount of reactants necessary to obtain a desired rate of reaction.

In general, the processes of this invention may be conducted at a reaction temperature from about −25° C. or lower to about 200° C. The preferred reaction temperature employed in a given process will, of course, be dependent upon the particular starting material and optically active metal-ligand complex catalyst employed as well as the efficiency desired. Lower reaction temperatures may generally tend to favor higher ee. For example, asymmetric epoxidations at reaction temperatures of about −20° C. to about 120° C. are preferred for all types of olefinic starting materials. More preferably, alpha-olefins can be effectively epoxidated at a temperature of from about 0° C. to about 90° C. while even less reactive olefins than conventional linear alpha-olefins and internal olefins, as well as mixtures of alpha-olefins and internal olefins, are effectively and preferably epoxidated at a temperature of from about 0° C. to about 50° C.

The processes are conducted for a period of time sufficient to produce the optically active products. The exact time employed is dependent, in part, upon factors such as temperature, nature, and proportion of starting materials, and the like. The reaction time will normally be within the range of from about one-half to about 200 hours or more, and preferably from less than about 1 to 10 hours.

The asymmetric syntheses process (for example, asymmetric epoxidation process) of this invention can be carried out in either the liquid or gaseous state and involve a batch, continuous liquid or gas recycle system, or combination of such systems. A batch system is preferred for conducting the processes of this invention. Preferably, asymmetric epoxidation of this invention involves a batch homogeneous catalysis process wherein the epoxidation is carried out in the presence of any suitable conventional solvent as further outlined herein.

The asymmetric syntheses processes of this invention may be conducted in the presence of an organic solvent for the optically active metal-ligand complex catalyst. Depending on the particular catalyst and reactants employed, suitable organic solvents include, for example, alcohols, alkanes, alkenes, alkenes, ethers, aldehydes, ketones, esters, acids, amides, amines, aromatics, and the like. Any suitable solvent which does not unduly adversely interfere with the intended asymmetric syntheses process can be employed and such solvents may include those heretofore commonly employed in known metal catalyzed processes. Increasing the dielectric constant or polarity of a solvent may generally tend to favor increased reaction rates.

Mixtures of one or more different solvents may be employed if desired. It is obvious that the amount of solvent is not critical to the subject invention and need only be that amount sufficient to provide the reaction medium with the particular metal concentration desired for a given process. In general, the amount of solvent when employed may range from about 5% by weight up to about 95% by weight or more, based on the total weight of the reaction medium.

The processes of this invention are useful for preparing substituted and unsubstituted optically active compounds. The processes of this invention stereo-selectively produce a chiral center. Illustrative optically active compounds prepared by the processes of this invention include, for example, substituted and unsubstituted alcohols or phenols; amines; amides; ethers or epoxides; esters; carboxylic acids or anhydrides; ketones; olefins; acetylenes; halides or sulfonates; aldehydes; nitriles; and hydrocarbons. Illustrative of suitable optically active compounds which can be prepared by the processes of this invention (including derivatives of the optically active compounds described hereinbelow and also prochiral and chiral starting material compounds as described hereinabove) include those permissible compounds which are described in Kirk-Othmer, Encyclopedia of Chemical Technology, Third Edition, 1984, the pertinent portions of which are incorporated herein by reference in their entirety, and The Merck Index, An Encyclopedia of Chemicals, Drugs, and Biologicals, Eleventh Edition, 1989, the pertinent portions of which are incorporated herein by reference in their entirety.

The processes of this invention can provide optically active products having very high enantioselectivity and regioselectivity, e.g., epoxidation. Enantiomeric excesses of preferably greater than 50% can be obtained by the processes of this invention. The processes of this invention can also be carried out at highly desirable reaction rates suitable for commercial use.

The desired optically active products, e.g., epoxidates, may be recovered in any conventional manner. Suitable separation techniques include, for example, solvent extraction, crystallization, distillation, vaporization, wiped film evaporation, falling film evaporation, and the like. It may be desired to remove the optically active products from the reaction systems as they are formed through the use of trapping agents as described in WO patent 88/08835.

The optically active products produced by the asymmetric syntheses processes of this invention can undergo further reaction(s) to afford desired derivatives thereof. Such permissible derivatization reactions can be carried out in accordance with conventional procedures known in the art. Illustrative derivatization reactions include, for example, esterification, oxidation of alcohols to aldehydes, N-alkylation of amides, addition of aldehydes to amides, nitrile reduction, acylation of ketones by esters, acylation of amines, and the like.

Illustrative of suitable reactants in effecting the asymmetric synthesis processes of this invention include by way of example:

| | |
|---|---|
| Al | alcohols |
| PH | phenols |
| THP | thiophenols |
| MER | mercaptans |
| AMN | amines |
| AMD | amides |
| ET | ethers |
| EP | epoxides |
| ES | esters |
| H | hydrogen |
| CO | carbon monoxide |
| HCN | hydrogen cyanide |
| HS | hydrosilane |
| W | water |
| GR | grignard reagent |
| AH | acyl halide |
| UR | ureas |
| OS | oxalates |
| CN | carbamates |
| CNA | carbamic acids |
| CM | carbonates |
| CMA | carbonic acids |
| CA | carboxylic acids |
| ANH | anhydrides |
| KET | ketones |
| OLE | olefins |
| ACE | acetylenes |
| HAL | halides |
| SUL | sulfonates |
| ALD | aldehydes |
| NIT | nitriles |
| HC | hydrocarbons |
| DZ | diazo compounds |
| BOR | boranes |
| ESE | enol silyl ethers |
| SUD | sulfides |

Illustrative of suitable optically active products prepared by the asymmetric syntheses processes of this invention include by way of example:

| | |
|---|---|
| Al | alcohols |
| PH | phenols |
| THP | thiophenols |
| MER | mercaptans |
| AMN | amines |
| AMD | amides |
| ET | ethers |
| EP | epoxides |
| ES | esters |
| H | hydrogen |
| CO | carbon monoxide |
| SI | silanes |
| UR | ureas |
| OX | oxalates |
| CN | carbamates |
| CNA | carbamic acids |
| CM | carbonates |
| CMA | carbonic acids |
| CA | carboxylic acids |
| ANH | anhydrides |
| KET | ketones |
| OLE | olefins |
| ACE | acetylenes |
| HAL | halides |
| SUL | sulfonates |
| ALD | aldehydes |
| NIT | nitriles |
| HC | hydrocarbons |
| CYP | cyclopropanes |
| ABR | alkylboranes |
| ADL | aldols |
| AZ | aziridines |
| SUO | sulfoxides |

Illustrative of asymmetric syntheses reactions encompassed within the scope of this invention include, for example, the following reactant/product combinations:

| REACTANTS(S) | PRODUCT(S) |
|---|---|
| OLE | EP |
| OLE, CO, H | ALD |
| OLE, CO, H | CA |
| ALD | KET |
| OLE, ALD | KET |
| OLE, HC | HC |
| OLE, CO | CA |
| OLE, CO, AMN | AMD |
| OLE | AZ |
| SUD | SUO |
| OLE, CO, AL | ES |
| KET, H | AL |
| EP, H | AL |
| OLE, AMN | AMN |
| OLE, AL | ET |
| AL, CO | HC |
| AL | ALD |
| OLE, HCN | NIT |
| OLE, HS | SI |
| OLE, CO, W | CA |
| OLE | OLE |
| GR | HC |
| AH | HAL |
| OLE, H | HC |
| OLE, BOR | AL |
| OLE, BOR | ABR |
| OLE, DZ | CYP |
| KET, AL | AL |
| ALD, ESE | ADL |
| KET, ESE | ADL |
| KET, HS | AL |
| EP, CO, H | ALD |
| EP, HCN | NIT |
| ALD | CA |

As indicated above, the processes of this invention can be conducted in a batch or continuous fashion, with recycle of unconsumed starting materials if required. The reaction can be conducted in a single reaction zone or in a plurality of reaction zones, in series, or in parallel, or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and the recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Finally, the optically active products of the process of this invention have a wide range of utility that is well known and documented in the prior art, e.g. they are especially useful as pharmaceuticals, flavors, fragrances, agricultural chemicals, and the like. Illustrative therapeutic applications include, for example, non-steroidal anti-inflammatory drugs, ACE inhibitors, beta-blockers, analgesics, bronchodilators, spasmolytics, antihistamines, antibiotics, antitumor agents, and the like.

As used herein, the following terms have the indicated meanings:

| | |
|---|---|
| Chiral | molecules which have one or more centers of asymmetry. |
| Achiral | molecules or processes which do not include or involve at least one center of asymmetry. |
| Prochiral | molecules which have the potential to be converted to a chiral product in a particular process. |
| Chiral Center | any structural feature of a molecule that is a site of asymmetry. |
| Racemic | a 50/50 mixture of two (2) enantiomers of chiral compound. |
| Stereoisomers | compounds which have identical chemical construction, but differ as regards the arrangement of the atoms or groups in space. |
| Enantiomer | stereoisomers which are non-superimposable mirror images of one another. |
| Stereoselective | a process which produces a paricular stereoisomer in favor of others. |
| Enantiomeric Excess (ee) | a measure of the relative amount of two (2) enantiomers present in a product. Enantiomeric excess may be calculated by the formula [amount of major enantiomer − amount of minor enantiomer]/[amount of major enantiomer + amount of minor enantiomer]. |
| Optical Activity | an indirect measurement of the relative amounts of stereoisomers present in a given product. Chiral compounds have the ability to rotate plane polarized light. When one enantiomer is present in excess over the other, the mixture is optically active. |
| Optically Active | a mixture of stereoisomers which rotates plane polarized light due to an excess of one of the stereoisomers over the others. |
| Optically Pure | a single stereoisomer which rotates plane polarized light |
| Regioisomers | compounds which have the same molecular formula but differing in the connectivity of the atoms. |
| Regioselective | a process which favors the production of a particular regioisomer over all others. |

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

Examples (General)

Gas chromatographic (GC) analyses were carried out on Hewlett Packard 5890 instruments equipped with FID detectors. The enantiomeric excesses of the epoxides were determined by chiral GC (Cyclodex B, Chiraldex G-PN) or HPLC (S,S-Whelk-0), or NMR in the presence of Eu(hfc)3. $^1$H and $^{13}$C NMR were recorded on Bruker NR200 or Bruker ARX400 spectrometer. Flash Column separations were accomplished using Merck silica gel (230–400 mesh) purchased from Aldrich. Mass spectra were recorded on a Finnigan SSQ 7000 mass spectrometer. The mass of the metal complexes were determined using LCMS with an atmospheric pressure CI interphase.

Example 1

Preparation of Ligand Precursor (1R,2R)-N-Picolinyl-1,2-Diphenylethylenediamine

A solution of (1R,2R)-1,2-diphenylethylenediamine (1.16 g, 4.74 mmol), picolinic acid (596 mg, 4.79 mmol, 1.01 eq.), N,N-dimethyl-4-aminopyridine (100 mg, 0.82 mmol, 0.17 eq.) and 1,3-dicyclohexycarbodiimide (1.07 g, 5.2 mmol, 1.1 eq.) in dichloromethane (40 ml) was stirred at room temperature under $N_2$ for 18 hours. The reaction mixture was filtered and washed with water. Column chromatography on silica gel using EtOAc/$CH_2Cl_2$ (4:1) afforded 1.06 g of white solids as title compound (71% yield). NMR and GCMS confirmed the structure.

Example 2

Preparation of Ligand Picolinamide-Salicylidene

A mixture of the monoamide (from Example 1) and salicylaldehyde in equal molar amounts in absolute ethanol (200 proof) was refluxed for three hours. TLC (EtOAc/$CH_2Cl_2$, 3/2) showed the disappearance of the monoamide and appearance of a less polar component (higher Rf). Removal of the ethanol on rotovap gave the desired ligand in quantitative yield. The crude product was pure by NMR and was used in the next step without purification.

Example 3

Preparation of Mn-Amide-Salicylidene Catalyst

The ligand from Example 2 (0.92 mmol) and Mn(OAc)3 dihydrate (4.86 mmol, 1.34 g, 5.2 eq.) were heated to reflux in 20 ml of 190 proof ethanol for 18 hours. TLC analysis (25% acetone in hexanes) showed almost complete disappearance of the ligand. After allowing the reaction to cool to 40° C., LiCl (4.66 mmol, 2 g, 5 eq.) was added and reflux was resumed for 2.5 hours. Ethanol was removed by rotovap and the residue was taken in $CH_2Cl_2$, and washed 2–3 times with half-saturated aqueous NaCl solution. The complex was isolated in 43% yield by column on silica gel using a mixture of 35% acetone in hexanes as eluent. Mass analysis showed molecular ion as follows:

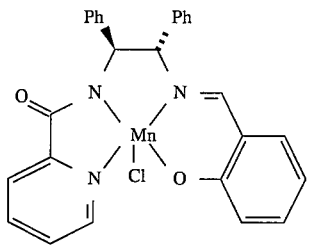

Examples 4–41

Epoxidation of Olefins

The following procedure was used to epoxidize the various olefins shown in Tables 1–8 by the catalysts indicated and which were prepped in Examples 1–3. The maganese complex (5–20 mg, 1–5 mol percent versus the olefin) was dissolved in 1–2 ml $CH_2Cl_2$ at room temperature. The olefin (~30 to 120 mg, 0.2 to 1.0 mmol) was added and the mixture was cooled to 0° C. In some cases, a known amount of decane was added as internal standard for GC analysis. Cold buffered bleach (0° C., pH=11, made from Clorox, 2 mL) was added at 0° C. and the reaction mixture was stirred at room temperate for 6–40 hours. The progress of the reaction was monitored by GC alysis. Hexane (2 mL) was added and the organic layer was separated and ee of the epoxide was analyzed by GC, LC, or NMR.

TABLE 1

Epoxidation of Olefins with Complex

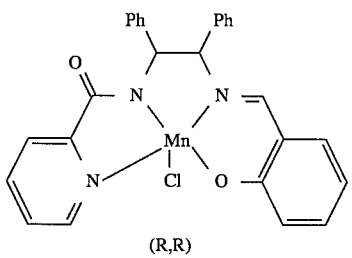

(R,R)

| Example Number | Substrate | Cat. mol % | Epoxides Ratio (cis/trans) | Epoxides ee (%) cis/trans |
|---|---|---|---|---|
| 4 | 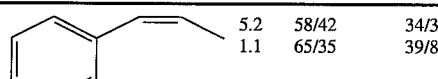 | 5.2 | 58/42 | 34/3 |
| 5 | | 1.1 | 65/35 | 39/8 |
| 6 | 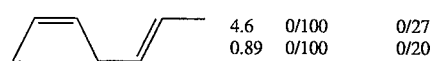 | 4.6 | 0/100 | 0/27 |
| 7 | | 0.89 | 0/100 | 0/20 |
| 8 | 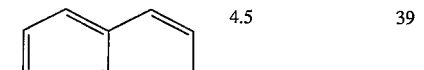 | 4.5 | | 39 |

TABLE 1-continued

Epoxidation of Olefins with Complex

[Mn complex structure with Ph, Ph groups, pyridine-carboxamide-salicylidene ligand, Cl, (R,R)]

| Example Number | Substrate | Cat. mol % | Epoxides Ratio (cis/trans) | Epoxides ee (%) cis/trans |
|---|---|---|---|---|
| 9 | indene | 4.7 | | 34 |
| 10 | indene | 0.97 | | 22 |

TABLE 2

Epoxidation of Olefins by Bleach with Complex

[Mn complex structure with Ph, Ph groups, pyridine-carboxamide-salicylidene ligand with t-butyl substituent, Cl, (R,R)]

| Example Number | Substrate | Cat. mol % | Epoxides Ratio (cis/trans) | Epoxides ee (%) cis/trans |
|---|---|---|---|---|
| 11 | cis-β-methylstyrene | 3.8 | 78/22 | 56/14 |
| 12 | trans-β-methylstyrene | 4.7 | 0/100 | 0/31 |
| 13 | dihydronaphthalene | 3.1 | | 46 |
| 14 | styrene | 3.5 | | 36 |

TABLE 2-continued

Epoxidation of Olefins by Bleach with Complex

[Mn complex structure with Ph, Ph groups, pyridine-carboxamide-salicylidene ligand with t-butyl substituent, Cl, (R,R)]

| Example Number | Substrate | Cat. mol % | Epoxides Ratio (cis/trans) | Epoxides ee (%) cis/trans |
|---|---|---|---|---|
| 15 | stilbene | 4.9 | | 15 |

TABLE 3

Epoxidation of Olefins with Complex

[Mn complex structure with Ph, Ph groups, pyridine-carboxamide-salicylidene ligand with two t-butyl substituents, Cl, (R,R)]

| Example Number | Substrate | Cat. mol % | Epoxides Ratio (cis/trans) | Epoxides ee (%) cis/trans |
|---|---|---|---|---|
| 16 | cis-β-methylstyrene | 3.3 (0° C.) | 88/12 | 62/10 |
| 17 | cis-β-methylstyrene | 3.1 (r.t) | 70/30 | 58/6 |
| 18 | trans-β-methylstyrene | 4.0 | 0/100 | 0/40 |
| 19 | dihydronaphthalene | 2.8 | | 50 |
| 20 | styrene | 4.1 | | 13 |

TABLE 3-continued

Epoxidation of Olefins with Complex

[Structure: Mn complex with pyridine-carboxamide-imine ligand, Ph,Ph diamine backbone, t-Bu on salicylidene, (R,R)]

| Example Number | Substrate | Cat. mol % | Epoxides Ratio (cis/trans) | Epoxides ee (%) cis/trans |
|---|---|---|---|---|
| 21 | [stilbene] | 4.5 | | 7 |
| 22 | [indene] | 4.7 | | 34 (with PPyO) |
| 23 | [indene] | 4.7 | | 28 |

TABLE 4

Epoxidation of Olefins with Complex

[Structure: Mn complex with t-Bu on pyridine ring, (R,R)]

| Example Number | Substrate | Cat. mol % | Epoxides Ratio (cis/trans) | Epoxides ee (%) cis/trans |
|---|---|---|---|---|
| 24 | [cis-β-methylstyrene] | 4.5 | 76/24 | 55/6 |
| 25 | [trans-stilbene] | 5.3 | 0/100 | 0/39 |

TABLE 4-continued

Epoxidation of Olefins with Complex

[Structure: Mn complex with t-Bu on salicylidene ring (different position), (R,R)]

| Example Number | Substrate | Cat. mol % | Epoxides Ratio (cis/trans) | Epoxides ee (%) cis/trans |
|---|---|---|---|---|
| 26 | [dihydronaphthalene] | 5.6 | | 50 |
| 27 | [styrene] | 3.3 | | 26 |

TABLE 5

Epoxidation of Olefins with Complex

[Structure: Mn complex with isopropyl on pyridine, t-Bu on salicylidene, (R,R)]

| Example Number | Substrate | Cat. mol % | Epoxides Ratio (cis/trans) | Epoxides ee (%) cis/trans |
|---|---|---|---|---|
| 28 | [cis-β-methylstyrene] | 5 | 84/16 | 37/21 |
| 29 | [trans-β-methylstyrene] | 5 | 0/100 | 0/27 |
| 30 | [dihydronaphthalene] | 5 | | 38 |

TABLE 5-continued

Epoxidation of Olefins with Complex

(R,R)

| Example Number | Substrate | Cat. mol % | Epoxides Ratio (cis/trans) | Epoxides ee (%) cis/trans |
|---|---|---|---|---|
| 31 | PhCH=CHCH3 | 5 | | 25 |

TABLE 6

Epoxidation of Olefins by Bleach with Complex

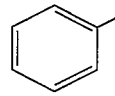

(R,R)

| Example Number | Substrate | Cat. mol % | Epoxides Ratio (cis/trans) | Epoxides ee (%) cis/trans |
|---|---|---|---|---|
| 32 | cis-PhCH=CHCH3 | 5.7 | 70/30 | 36/15 |
| 33 | trans-PhCH=CHCH3 | 4.4 | 0/100 | 0/33 |
| 34 | dihydronaphthalene | 4.5 | | 41 |
| 35 | styrene | 3.6 | | 13 |

TABLE 7

Epoxidation of Olefins with Complex

| Example Number | Substrate | Cat. mol % | Epoxides Ratio (cis/trans) | Epoxides ee (%) cis/trans |
|---|---|---|---|---|
| 36 | cis-PhCH=CHCH3 | 4.8 | 32/68 | 14/3 |
| 37 | dihydronaphthalene | 5.1 | | 27 |

TABLE 8

Epoxidation of Olefins by Bleach with Complex

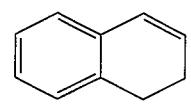

(R,R)

| Example Number | Substrate | Cat. mol % | Epoxides Ratio (cis/trans) | Epoxides ee (%) cis/trans |
|---|---|---|---|---|
| 38 | cis-PhCH=CHCH3 | 4.1 | 67/33 | 9/30 |
| 39 | trans-PhCH=CHCH3 | 5.5 | 0/100 | 0/35 |
| 40 | dihydronaphthalene | 4.7 | | 26 |

TABLE 8-continued

Epoxidation of Olefins by Bleach with Complex

[Structure of (R,R) Mn complex with pyridine-carboxamide and tert-butyl salicylaldimine ligands, Cl ligand]

(R,R)

| Example Number | Substrate | Cat. mol % | Epoxides Ratio (cis/trans) | Epoxides ee (%) cis/trans |
|---|---|---|---|---|
| 41 | [styrene structure] | 1.5 | | 7 |

As previously mentioned, the novel catalysts have a wide range of applications and set forth below are examples of such utility.

Example 42

Asymmetric Hydrosilylation of Acetophenone

The catalyst (0.020 g) of Example 3 is charged to a 50 ml Schlenk flask under nitrogen. Tetrahydrofuran (THF) (5.0 ml) is added to dissolve the catalyst. 0.58 ml of acetophenone and 0.93 ml of diphenylsilane are added to the flask via syringe. The solution is stirred under nitrogen for 18 hours. The solution is treated with 10 ml of 10% hydrochloric acid and is extracted two times with 10 ml of diethyl ether. This solution is analyzed by GC on a Chiraldex B-PH column which can separate the two enantiomers of the resulting sec-phenethyl alcohol. This analysis indicates an 80:20 ratio of the R and S enantiomers for an ee of 60%.

Example 43

Asymmetric Hydrocyanation of Styrene

The catalyst (0.15 g) of Example 3 is charged to a 50 ml Schlenk flask under nitrogen. Deoxygenated THF (10 ml) is added, and the solution is stirred for 30 minutes. 2.0 ml of styrene and 2.00 ml of acetone cyanohydrin are added to the flask via syringe. The solution is stirred for 24 hours at 25° C.

A portion of this solution is analyzed by GC to determine product composition. An isomer ratio of 2:1 (α-methylbenzyl cyanide:hydrocinnamonitrile) is observed. A second portion of this solution is analyzed by GC on a Chiraldex G-TA column which can separate the two enantiomers of the resulting α-methylbenzyl cyanide. This analysis indicates an 82:18 ratio of the enantiomers for an ee of 64%.

Example 44

Asymmetric Transfer Hydrogenation of Acetophenone

The catalyst (0.020 g) of Example 3 is charged to a 50 ml Schlenk flask under nitrogen. THF (5.0 ml) is added to dissolve the catalyst. To this solution is added 5.0 ml of 2-propanol, 0.58 ml of acetophenone, and 0.012 g of potassium hydroxide. The solution is stirred under nitrogen for 24 hours. This reaction mixture is analyzed by GC on a Chiraldex B-PH column which can separate the two enantiomers of the resulting sec-phenylethyl alcohol. This analysis indicates a 60:40 ratio of the S and R enantiomers for an ee of 20%.

Example 45

Asymmetric Hydroboration of Styrene

The catalyst (0.050 g) of Example 3, excluding acetone, is charged to a 50 ml Schlenk flask under nitrogen. Distilled 1,2-dimethoxyethane (2.0 ml) is added to the flask. 0.23 ml of styrene and 0.23 ml of catecholborane are added to the flask via syringe. The solution is stirred under nitrogen for two hours. The solution is treated with 4 ml of methanol, 4.8 ml of 3.0 mol/liter sodium hydroxide solution, and 0.52 ml of 30% hydrogen peroxide. The solution is stirred for three hours and is extracted with 10 ml of diethyl ether. A portion of this solution is analyzed by GC to determine product composition. An isomer ratio of 3:1 (sec-phenethyl alcohol:2-phenylethanol) is observed. A second portion of this solution is analyzed by GC on a Chiraldex B-PH column which can separate the two enantiomers of the resulting sec-phenethyl alcohol. This analysis indicates a 61:39 ratio of the S and R enantiomers for an ee of 22%.

Example 46

Asymmetric Cyclopropanation of Styrene

The catalyst (0.085 g) of Example 3 is charged to a 25 ml Schlenk flask under nitrogen. Toluene (5.0 ml) is added to the flask under nitrogen. 0.10 ml of triethylamine is added to the flask via syringe, and the solution is stirred under nitrogen for 15 minutes. 5.0 ml of styrene is added by syringe followed by 0.250 ml of ethyldiazoacetate. The solution is stirred under nitrogen for two hours. A portion of the reaction mixture is analyzed by GC to determine product composition. An isomer ratio of 2.1:1 (trans:cis) is observed for the product cyclopropanes. A second portion of this solution is analyzed by GC on a Chiraldex B-PH column which can separate the two enantiomers of the resulting cis-ethyl-2-phenylcyclopropanecarboxylate. This analysis indicates a 63:37 ratio of the cis cyclopropane enantiomers for an ee of 26%.

Example 47

Asymmetric Aldol Condensation of Benzaldehyde & Methyl Trimethylsilyl Dimethylketene Acetal The catalyst (0.050 g) of Example 3 is charged to a 50 ml Schlenk flask under nitrogen. Dichloromethane (2.0 ml) is added to the flask under nitrogen. 0.20 ml of benzaldehyde and 0.40 ml of methyl trimethylsilyl dimethylketene acetal is added to the flask via syringe. The solution is stirred under nitrogen for 18 hours. The solution is treated with 10 ml of 10% hydrochloric acid and is extracted two times with 10 ml of diethyl ether. This solution is analyzed by GC on a Chiraldex B-PH column which can separate the two enantiomers of the resulting methyl-2,2-dimethyl-3-phenyl-3-trimethylsiloxypropionate. This analysis indicates a 75:25 ratio of the enantiomers for an ee of 76%.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process which comprises reacting a prochiral or chiral compound in the presence of an optically active metal-ligand complex catalyst, in enantiomeric form, to produce an optically active product, said optically active metal-ligand complex catalyst having the formula:

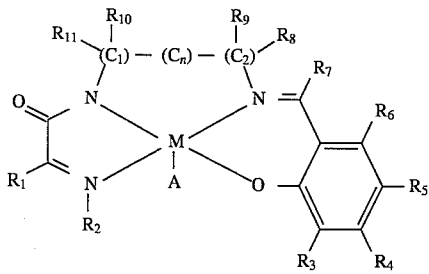

wherein $R_1$ and $R_2$ are independently selected from the group consisting of hydrogen, substituted or unsubstituted alkyl $C_1$–$C_{50}$; substituted and unsubstituted phenyl, naphthyl, and anthracyl, and a cyclic ring encompassing both $R_1$ and $R_2$ and containing a total of 3 to 50 atoms selected from the group consisting of carbon atoms, oxygen atoms, nitrogen atoms, sulfur atoms, and mixtures thereof, with the proviso that the substituents on the alkyl, phenyl, naphthyl, anthracyl, and cyclic rings can be nitro, halogen, alkoxy, carboxylate, amino, amide, silyl, and siloxyl; $R_3$–$R_8$ and $R_{11}$ are independently selected from the group consisting of substituted or unsubstituted alkyl and aryl; nitro; halogen; hydrogen; alkoxy; carboxylate; amino; amide; silyl; and siloxyl; $R_4$ and $R_5$, $R_5$ and $R_6$, and $R_6$ and $R_7$ may also (in addition to the above) form a cyclic ring containing a total of 2 to 6 atoms selected from the group consisting of carbon atoms, oxygen atoms, nitrogen atoms, sulfur atoms, and mixtures thereof and said ring can be substituted or unsubstituted; $R_9$ and $R_{10}$ are independently selected from the group consisting of hydrogen; alkyl $C_1$–$C_{20}$; substituted and unsubstituted phenyl, naphthyl, and anthracyl; and a cyclic ring encompassing both $R_9$ and $R_{10}$ and containing a total of 2 to 6 atoms selected from the group consisting of carbon atoms, oxygen atoms, nitrogen atoms, sulfur atoms, and mixtures thereof; M is a transition metal ion; A is an anion; n is either 0, 1, or 2; and $(C^1)$, $(C^n)$, and $(C^2)$ are independently or jointly part of an unsubstituted or substituted aryl group.

2. The process as set forth in claim 1 wherein M is selected from the group consisting of manganese, cobalt, nickel, iron, rhenium, ruthenium, rhodium, chromium, technetium, palladium, platinum, osmium, copper, tellurium, titanium, vanadium, molybdenum, and gadolinium.

3. The process as set forth in claim 1 wherein M is manganese.

4. The process as set forth in claim 1 wherein A is selected from the group consisting of halide, acetate, sulfonate, triflate, tosylate, carboxylate, $PF_6$, $BF_4$, $B(R)_4$, and R wherein R is either alkyl or substituted or unsubstituted aryl.

5. The process as set forth in claim 1 wherein A is chlorine.

6. The process as set forth in claim 1 wherein $R_9$ and $R_{10}$ collectively form part of a cyclic ring which is phenyl.

7. The process as set forth in claim 1 wherein $R_9$ and $R_{10}$ are both phenyl groups.

8. The process as set forth in claim 1 wherein said catalyst is non-chiral.

9. The process as set forth in claim 1 wherein said catalyst is chiral.

10. The process as set forth in claim 1 wherein either one or both of $(C^1)$ and $(C^2)$ are a chiral carbon center.

11. The process as set forth in claim 4 wherein the halide is selected from the group consisting of chlorine, bromine, fluorine, and iodine.

12. The process as set forth in claim 1 wherein $(C_n)$, n=0, M is manganese; $R_5$ is t-butyl; $R_8$ and $R_{11}$ are hydrogen; $R_9$ and $R_{10}$ are both phenyl; $R_3$ is 1,1-diethylpropyl.

13. The process as set forth in claim 1 wherein said catalyst is substantially in its SS enantiomeric form.

14. The process as set forth in claim 1 wherein said catalyst is substantially in its RR enantiomeric form.

15. The process of claim 1 which comprises an epoxidation, hydroacylation (intramolecular and intermolecular), hydrocyanation, hydrosilylation, hydrocarboxylation, hydroamidation, hydroesterification, hydrogenolysis, aminolysis, alcoholysis, carbonylation, decarbonylation, isomerization, transfer hydrogenation, hydroboration, cyclopropanation, aldol condensation, allylic alkylation, codimerization, Diels-Alder or Grignard cross coupling process.

16. The process of claim 1 in which the prochiral or chiral compound is selected from the group consisting of substituted or unsubstituted olefin, aldehyde, ketone, epoxide, alcohol, amine, and Grignard reagent.

17. The process of claim 1 in which the optically active product is selected from the group consisting of substituted or unsubstituted aldehyde, ketone, carboxylic acid, amide, epoxide, ester, alcohol, amine, and ether.

18. The process of claim 1 in which the optically active product has an enantiomeric excess of greater than 50%.

19. The process of claim 1 further comprising derivatizing the optically active product.

20. The process of claim 10 in which the derivatizing reaction comprises an oxidation, reduction, condensation, amination, esterification, alkylation, or acylation reaction.

21. An optically active product produced by the process of claim 1.

22. The process as set forth in claim 15 wherein the process is epoxidation.

23. The process as set forth in claim 22 wherein the compound is an olefin.

24. The process as set forth in claim 23 wherein the olefin is unfunctionalized.

25. The process as set forth in claim 23 wherein the olefin is selected from the group consisting of a substituted or unsubstituted olefin, or a substituted or unsubstituted olefin comprising p-isobutylstyrene, 2-vinyl-6-methoxynaphthalene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether and vinyl chloride.

26. A method of enantioselectively epoxidizing a prochiral olefin with the use of a chiral catalyst comprising the steps of providing a prochiral olefin, providing an oxygen atom source, providing a chiral catalyst, and reacting said olefin, said oxygen atom source, and said chiral catalyst under such conditions and for such time sufficient to epoxidize said olefin, said catalyst having the formula:

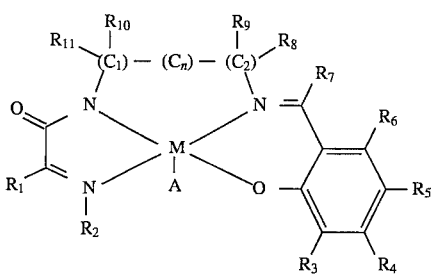

wherein $R_1$ and $R_2$ are independently selected from the group consisting of hydrogen, substituted or unsubstituted alkyl $C_1$–$C_{50}$; substituted and unsubstituted phenyl, naphthyl, and anthracyl, and a cyclic ring encompassing both $R_1$ and $R_2$ and containing a total of 3 to 50 atoms selected from the group consisting of carbon atoms, oxygen atoms, nitrogen atoms, sulfur atoms, and mixtures thereof, with the proviso that the substituents on the alkyl, phenyl, naphthyl, anthracyl, and cyclic rings can be nitro, halogen, alkoxy, carboxylate, amino, amide, silyl, and siloxyl; $R_3$–$R_8$ and $R_{11}$ are independently selected from the group consisting of substituted or unsubstituted alkyl and aryl; nitro; halogen; hydrogen; alkoxy; carboxylate; amino; amide; silyl; and siloxyl; $R_4$ and $R_5$, $R_5$ and $R_6$, and $R_6$ and $R_7$ may also (in addition to the above) form a cyclic ring containing a total of 2 to 6 atoms selected from the group consisting of carbon atoms, oxygen atoms, nitrogen atoms, sulfur atoms, and mixtures thereof and said ring can be substituted or unsubstituted; $R_9$ and $R_{10}$ are independently selected from the group consisting of hydrogen; alkyl $C_1$–$C_{20}$; substituted and unsubstituted phenyl, naphthyl, and anthracyl; and a cyclic ring encompassing both $R_9$ and $R_{10}$ and containing a total of 2 to 6 atoms selected from the group consisting of carbon atoms, oxygen atoms, nitrogen atoms, sulfur atoms, and mixtures thereof; M is a transition metal ion; A is an anion; n is either 0, 1, or 2; and ($C^1$), ($C^n$), and ($C^2$) are independently or jointly part of an unsubstituted or substituted aryl group.

27. The process as set forth in claim 26 wherein M is selected from the group consisting of manganese, cobalt, nickel, iron, rhenium, ruthenium, rhodium, chromium, technetium, palladium, platinum, osmium, copper, tellurium, titanium, vanadium, molybdenum, and gadolinium.

28. The process as set forth in claim 26 wherein M is manganese.

29. The process as set forth in claim 26 wherein A is selected from the group consisting of halide, acetate, sulfonate, triflate, tosylate, carboxylate, $PF_6$, $BF_4$, $B(R)_4$, and R wherein R is either alkyl or substituted or unsubstituted aryl.

30. The process as set forth in claim 26 wherein A is chlorine.

31. The process as set forth in claim 26 wherein $R_9$ and $R_{10}$ collectively form part of a cyclic ring which is phenyl.

32. The process as set forth in claim 26 wherein $R_9$ and $R_{10}$ are both phenyl groups.

33. The process as set forth in claim 26 wherein either one or both of ($C^1$) and ($C^2$) are a chiral carbon center.

34. The process as set forth in claim 29 wherein the halide is selected from the group consisting of chlorine, bromine, fluorine, and iodine.

35. The method of claim 26 wherein the prochiral olefin is selected from the group consisting of monosubstituted and cis 1,2-disubstituted olefins.

36. The method of claim 26 wherein the prochiral olefin is a cis disubstituted olefin bearing a primary substituent on one side of the double bond and a secondary, tertiary, or aryl substituent on the other side.

37. The method of claim 26 wherein the olefin is selected from the group consisting of cis-β-methylstyrene, dihydronaphthalene, 2-cyclohexenyl-1,1-dioxolane, 2,2-dimethylchromene, styrene, and propylene.

38. The method of claim 26 wherein the oxygen atom source is selected from the group consisting of NaOCl, iodosomesitylene, $NaIO_4$, $NBu_4IO_4$, potassium peroxymonosulfate, magnesium monoperoxyphthalate, and hexacyanoferrate ion.

39. The method of claim 26 wherein the oxygen atom source is selected from the group consisting of NaOCl and iodosomesitylene.

40. The method of claim 26 wherein the oxygen atom source is NaOCl.

* * * * *